United States Patent
Rebollo Garcia et al.

(10) Patent No.: US 9,644,001 B2
(45) Date of Patent: *May 9, 2017

(54) CELL-PENETRATING PEPTIDES

(71) Applicants: Universite Pierre et Marie Curie (Paris 6), Paris (FR); Institut Curie, Paris (FR)

(72) Inventors: Angelita Rebollo Garcia, Paris (FR); Fariba Nemati, Paris (FR); Didier Decaudin, Verrieres le Buisson (FR); Jeronimo Bravo Sicilia, Valencia (ES); Jesus Maria Fominaya Gutierrez, Madrid (ES)

(73) Assignees: Universite Pierre Et Marie Curie (Paris 6), Paris (FR); Institut Curie, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,754

(22) Filed: May 26, 2016

(65) Prior Publication Data

US 2016/0257713 A1 Sep. 8, 2016

Related U.S. Application Data

(63) Continuation of application No. 14/366,199, filed as application No. PCT/EP2012/076968 on Dec. 27, 2012, now Pat. No. 9,353,155.

(30) Foreign Application Priority Data

Dec. 27, 2011 (EP) .................................. 11306784

(51) Int. Cl.
| | |
|---|---|
| *A61K 38/00* | (2006.01) |
| *A61K 38/10* | (2006.01) |
| *A61K 38/04* | (2006.01) |
| *A61K 38/16* | (2006.01) |
| *C07K 7/08* | (2006.01) |
| *C07K 14/47* | (2006.01) |
| *C07K 7/06* | (2006.01) |
| *C12N 9/64* | (2006.01) |
| *C12N 7/00* | (2006.01) |
| *A61K 48/00* | (2006.01) |

(52) U.S. Cl.
CPC .................. *C07K 7/06* (2013.01); *C07K 7/08* (2013.01); *C07K 14/4747* (2013.01); *C12N 7/00* (2013.01); *C12N 9/6472* (2013.01); *C12Y 304/22062* (2013.01); *A61K 38/00* (2013.01); *A61K 48/00* (2013.01); *C07K 2319/00* (2013.01); *C07K 2319/10* (2013.01); *C07K 2319/31* (2013.01)

(58) Field of Classification Search
CPC ........ A61K 38/00; A61K 38/10; A61K 38/04; A61K 38/16; C07K 14/4747; C07K 2319/10; C07K 2319/31; C07K 7/08; C07K 14/47
USPC ..... 530/327, 324; 514/21.5, 18.9; 435/320.1
See application file for complete search history.

(56) References Cited

U.S. PATENT DOCUMENTS

| 8,957,184 B2 | 2/2015 | Rebollo Garcia et al. |
| 2006/0014930 A1* | 1/2006 | Garcia ................. C07K 14/005 530/326 |

FOREIGN PATENT DOCUMENTS

| WO | WO-2004/011595 | 2/2004 |
| WO | WO-2006/124537 | 11/2006 |

OTHER PUBLICATIONS

Diss et al "Heterotrimeric Coiled Coils with Core Residue Urea Side Chains" Journal of Organic Chemistry vol. 73, 2008.
Dujon et al "Genome Evolution in Yeasts" Nature: International Weekly Journal of Science vol. 430, 2004.
McDermott et al "The Mitochondrial Genome of a Cytoplasmic Male Sterile Line of Perennial Ryegrass (*Lollum perenne* L.) Contains an Integrated Linear Plasmid-Like Element" Theoretical and Applied Genetics: International Journal of Plan Breeding Research vol. 119, 2008.
Vives et al "Cell-Penetrating and Cell-Targeting Peptides in Drug Delivery" Reviews on Cancer vol. 1786, 2008.
Warner et al "The Light Gene of *Drosophilia melanogaster* Encodes a Homologue of VPS41, a Yeast Gene Involved in Cellular-Protein Trafficking" Genome vol. 41, 1998.

* cited by examiner

*Primary Examiner* — Julie Ha
(74) *Attorney, Agent, or Firm* — Cesari and McKenna LLP

(57) ABSTRACT

A vector that includes a cell-penetrating peptide linked to a therapeutic agent. The therapeutic agent can be a cytotoxic agent, an anti-viral agent, an anti-bacterial agent, or an anti-parasitic agent.

6 Claims, 3 Drawing Sheets

CELL-PENETRATING PEPTIDES

CROSS-REFERENCE TO RELATED APPLICATIONS

This application is a continuation of U.S. application Ser. No. 14/366,199, filed on Jun. 17, 2014, which is the National Stage of International Application No. PCT/EP2012/076968, filed on Dec. 27, 2012, which claims the benefit of European Application No. 11306784.7, filed on Dec. 27, 2011. The content of each prior application is hereby incorporated by reference in its entirety.

The invention relates to shuttle peptides that penetrate the cell membrane.

BACKGROUND

Apoptosis is a genetically programmed cell death and its deregulation is associated among other pathologies, with cancer. While apoptosis is known to rely on the Bcl-2 family members and caspases, recent data suggested that two major families of serine/threonine phosphatases, PP1 and PP2A, are key actors involved in cell life or cell death decision. The Ser/Thre phosphatase PP2A has been implicated in both, induction and prevention of apoptosis, pointing to a complex interplay of phosphatase actions. Several phosphatases have recently become attractive targets for the treatment of a variety of diseases, including cancers. However, the only clinical drugs targeting a phosphatase are the immunosuppressive cyclosporine A and FK506.

Cell penetrating peptides (CPP) are molecules which can translocate into cells without causing membrane damage, leading to their proposed use as vectors for delivering therapeutic cargo. Several CPP have been identified such as Tat, antennapedia, or SHV1 VP22. These peptides can cross the cell membrane and reach the cytoplasm and/or the nucleus. Penetrating peptides interacting with PP1/PP2A proteins were designed. This approach, named "Drug Phosphatase Technology" (DPT), was described in Guergnon et al, 2006 and International patent applications WO2003/011898 and WO2004/011595. A pro-apoptotic peptide, called DPT-C9h, that specifically deregulates the interaction between caspase-9 and PP2A, used this penetrating sequence (international patent application WO2010/112471).

However this peptide shows a short half-life, which is a real draw-back for clinical uses.

SUMMARY

The present mutated peptides overcome this problem since they are not digested by human serum proteases. This new property makes it possible to reduce the dose of peptide injected as well as the schedule of administration.

The invention provides a peptide comprising the following amino acid sequence (I):

$X_1$-KKKIK-Ψ-EI-$X_2$-$X_3$(I) (SEQ ID NO:1)

wherein $X_1$ is vacant, is a lysine residue, or valine-lysine;
$X_2$ is vacant, is a lysine residue, or lysine-isoleucine;
$X_3$ is vacant or is an amino acid sequence of 1 to 4 amino acids;
and Ψ is an amino acid residue that is different from arginine,
or a proteolysis-resistant peptide deriving from sequence (I) by one or more chemical modifications, or a substantially homologous peptide deriving from sequence (I) by one or more conservative substitutions.

The invention further provides a vector comprising said peptide, as a cell penetrating peptide, coupled to a molecule of interest.

The invention further provides a chimeric peptide construct, comprising said peptide, as a cell penetrating peptide, fused to a pro-apoptotic peptide, wherein the penetrating peptide is preferably fused at the N-terminus of the pro-apoptotic peptide.

Another aspect of the invention is a nucleic acid comprising a sequence coding for the cell penetrating peptide or for the chimeric peptide construct.

Still another aspect of the invention is a vector comprising a nucleic acid comprising (i) a nucleotide sequence coding for the cell penetrating peptide coupled to (ii) a nucleotide sequence of interest, for use in gene therapy or gene transfer in vivo or ex vivo.

Using the chimeric peptide construct, or of a nucleic acid encoding said chimeric peptide construct, for inhibition of cell proliferation in vitro, is further encompassed.

A further subject of the invention is a pharmaceutical composition comprising said vector or a chimeric peptide as herein described, in association with a pharmaceutically acceptable carrier.

The invention further relates to the use of the chimeric peptides or the pharmaceutical composition according to the invention for treating hyperproliferative diseases or parasitic diseases.

DETAILED DESCRIPTION

The inventors have worked to improve stability of the peptides disclosed in WO2010/112471, in particular peptide DPT-C9h that is subjected to degradation by proteases. This peptide corresponds to a penetrating peptide associated to the sequence of the binding site of caspase-9 to PP2A. This peptide induces apoptosis in human cell lines. In addition, it has a specific apoptotic effect only in tumoral B cells isolated from chronic lymphocityc leukemia patients without effect on healthy cells. In addition, the peptide induces important reduction in the size of tumor when injected in mice bearing human breast cancer xenograft.

DPT-C9 consists of sequence VKKKKIKREIKI-YVETLDDIFEQWAHSEDL (SEQ ID NO:6), where VKK-KKIKREIKI (SEQ ID NO:7) is the penetrating peptide.

The inventors have shown that a mutation in the penetrating peptide dramatically increases the stability of the whole peptide, while maintaining its properties, in particular its ability to induce apoptosis.

According to the invention, a mutation of the arginine residue in the penetrating peptide prevents cleavage from proteases.

The inventors have thus designed peptides comprising the following amino acid sequence (1):

$X_1$-KKKIK-Ψ-EI-$X_2$-$X_3$ (I) (SEQ ID NO:1)

wherein $X_1$ is vacant, is a lysine residue, or valine-lysine:
$X_2$ is vacant, is a lysine residue, or lysine-isoleucine:
$X_3$ is vacant or is an amino acid sequence of 1 to 4 amino acids;
and Ψ is an amino acid residue that is different from arginine.

In a preferred embodiment, Ψ is A, K or N. Still preferably Ψ is non-conservative with respect to arginine. In a preferred embodiment, Ψ is thus an amino acid residue different from lysine, asparagine, or glutamine. Preferably Ψ is alanine.

In a preferred embodiment.

$X_1$ is valine-lysine;

$X_2$ is lysine-isoleucine:

and $X_3$ is vacant.

The preferred peptide is VKKKKIKAEIKI (SEQ ID NO:2).

Another peptide is VKKKKIKKEIKI (SEQ ID NO:10).

Still another peptide is VKKKKIKNEIKI (SEQ ID NO: 11).

DEFINITIONS

The term "patient" refers to a human or non human animal, preferably a mammal, including male, female, adult and children in need of a treatment wherein a pro-apoptotic effect is desired.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "penetrating peptide" or "cell-penetrating peptide" (or "CPP") or "shuttle peptide", as used interchangeably, means that the peptide is able to translocate into cells without causing substantial membrane damage, and can be used as a vector of other molecules when linked to them. The terms refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refers to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. This property may be assessed by various methods known by the skilled person.

Two amino acid sequences are "homologous", "substantially homologous" or "substantially similar" when one or more amino acid residues are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |

TABLE 3-continued

Conservative Substitutions III

| Original Residue | Exemplary Substitution |
|---|---|
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Peptide Preparation:

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloyycarbonyl), Bzl (benzyl), Fmoc (9-fluorenylmethoxycarbonyl), Mbh (4, 4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid and/or a genetic construct, comprising or consisting of a nucleotidic sequence encoding a peptide according to the invention, polynucleotides with nucleotidic sequences complementary to one of the above sequences and sequences hybridizing to said polynucleotides under stringent conditions.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

Thus, in another aspect, the invention relates to a host or host cell that expresses (or that under suitable circumstances is capable of expressing) a peptide of the invention; and/or that contains a polynucleotide of the invention or genetic construct of the invention.

The method of producing the peptide may optionally comprise the steps of purifying said peptide, chemically modifying said peptide, and/or formulating said peptide into a pharmaceutical composition.

Chimeric Constructs:

The peptide $X_1$-KKKIK-$\Psi$-EI-$X_2$-$X_3$(1) (SEQ ID NO:1) is useful in the invention as cell penetrating peptide (CPP).

The invention thus provides vectors, comprising said peptide, as a cell penetrating peptide, coupled to a molecule of interest.

The molecule of interest may be coupled to one or several such CPP.

The molecule of interest may be any therapeutic agent, including a cytotoxic agent (preferably a pro-apoptotic peptide), an anti-viral agent, or anti-bacterial, or anti-parasitic agent.

In a preferred embodiment, chimeric peptide constructs, comprising said peptide, as a penetrating peptide, fused to a pro-apoptotic peptide, can be prepared.

Preferably the pro-apoptotic peptide is fused at the C-term of the penetrating peptide.

The pro-apoptotic peptide may be of any pro-apoptotic peptide of interest.

The chimeric peptide construct may preferably have a length comprised between 23 to 70 amino acids, preferably between 23 to 40 amino acids.

In a preferred embodiment, the pro-apoptotic peptide is a fragment of caspase-9 protein.

According to one embodiment, chimeric peptide constructs useful in the invention comprise, or consist in the following amino acid sequence:

Y-$X_{4a}$-ETLD-$X_{4b}$-I-$X_5$-EQWA-$X_6$-S-$X_7$ (SEQ ID NO:3) wherein $X_{4a}$ is valine or isoleucine;

$X_{4b}$ is aspartic acid or glycine;

$X_5$ is phenylalanine or leucine:

$X_6$ is arginine or histidine;

$X_7$ is vacant or is glutamate, or glutamate-aspartate, or glutamate-aspartate-leucine; or a proteolysis-resistant peptide deriving from said pro-apoptotic peptide by one or more chemical modifications, or a substantially homologous peptide deriving from SEQ ID NO:3 by one or more conservative substitutions.

Such proteolysis-resistant or homologous peptides induce cell apoptosis, in vitro and/or in vivo. Assays for determining if a molecule, for instance a peptide, induces cell apoptosis are well-known in the art and include, for instance, incubating cells with the candidate peptide and determining if apoptosis is induced by said candidate peptide, e.g. by Annexin V and PI labelling of cells and identifying as apoptotic cells, those being Annexin V$^+$ and PI$^-$.

In a preferred embodiment.

$X_{4a}$ is valine;

$X_{4b}$ is aspartic acid;

$X_5$ is phenylalanine;

and $X_6$ is histidine.

In a particular embodiment, the chimeric peptide construct is (SEQ ID NO: 4)
VKKKKIKAEIKI-YVETLDDIFEQWAHSEDL also herein designated Mut3-DPT-C9h.

In another particular embodiment, the chimeric peptide construct is (SEQ ID NO: 5)
VKKKKIKAEIKI-YIETLDDILEQWARSEDL In another particular embodiment, the chimeric peptide construct is (SEQ ID NO: 12)
VKKKKIKKEIKI-YVETLDDIFEQWAHSEDL also herein designated Mut1-DPT-C9h.

In another particular embodiment, the chimeric peptide construct is (SEQ ID NO: 13)
VKKKKIKKEIKI-YIETLDDILEQWARSEDL In a particular embodiment, the chimeric peptide construct is (SEQ ID NO: 14)
VKKKKIKNEIKI-YVETLDDIFEQWAHSEDL also herein designated Mut2-DPT-C9h.

In still another particular embodiment, the chimeric peptide construct is (SEQ ID NO: 15)
VKKKKIKNEIKI-YIETLDDILEQWARSEDL In still another embodiment, the pro-apoptotic peptide is a PP2Ah peptide that comprises or consists of:
a) the amino acid sequence DTLDHIRALDRLQEVPHEGP (SEQ ID NO:8);
b) an amino acid sequence substantially homologous to SEQ ID NO:8, preferably at least 80% identical to SEQ ID NO:8, which induces cell apoptosis; or
c) a proteolysis-resistant peptide which induces cell apoptosis and which derives from the peptide defined in a) or b) by one or more chemical modifications.

In a preferred embodiment, the pro-apoptotic peptide comprises or consists of the sequence DTLDHIRALDRLQEVPHEGP (SEQ ID NO: 9).

In a particular embodiment, the chimeric peptide construct is (SEQ ID NO: 16)
VKKKKIKAEIKI-DTLDHIRALDRLQEVPHEGP In another particular embodiment, the chimeric peptide construct is (SEQ ID NO: 17)
VKKKKIKKEIKI-DTLDHIRALDRLQEVPHEGP In still another particular embodiment, the chimeric peptide construct is (SEQ ID NO: 18)
VKKKKIKNEIKI-DTLDHIRALDRLQEVPHEGP Further Protection Against Proteolysis:

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH-bond.

For instance the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains, followed by chemical crosslinking of the chains, according to the so-called "staple" technology described in Walensky et al, 2004. For instance, amino acids at position i and i+4 to i+7 can be substituted by non-natural aminoacids that show reactive olefinic residues. All these proteolysis-resistant chemically-modified peptides are encompassed in the present invention.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Nucleic Acids

The invention also relates to a polynucleotide comprising or consisting of a nucleotide sequence encoding a peptide according to the invention.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the nucleic acid encoding the cell-penetrating peptide of the invention is coupled or fused to a nucleic acid that encodes a peptide or protein of interest. The peptide of interest may be a pro-apoptotic peptide as described herein. More generally it may the peptide or protein of interest may be any peptide or protein to express, such as therapeutic peptide or polypeptide, as well as any antigenic or immunogenic peptide if desired.

The nucleic acid may especially be carried by a viral vector, such as an adenovirus or a lentivirus, for ex vivo or in vivo infection and expression of the peptide or protein of interest coupled to the cell-penetrating peptide.

Pro-Apoptotic Activity:

The chimeric peptides as defined herein, or nucleic acids that encode said peptides, are useful for inhibition of cell proliferation in vitro or in vivo.

They are useful therapeutic agents, in particular for treating hyperproliferative diseases.

It is thus described a method of treatment of a hyperproliferative disease in a patient in need thereof, which method comprises administering said patient with the chimeric peptide construct, or a nucleic acid encoding said construct.

The peptides (or nucleic acids that encode said peptides) are useful for the treatment of a tumor, in particular a cancer tumor, preferably in a human patient.

The hyperproliferative disorder may be cancer, such as a haematologic cancer, in particular acute myelogenous leukaemia (AML), chronic lymphocytic leukaemia (CLL), multiple myeloma, Hodgkin's disease, non-Hodgkin's lymphoma, B cell, cutaneous T cell lymphoma, or a non-haematologic cancer, for instance brain, epidermoid (in particular lung, breast, ovarian), head and neck (squamous cell), bladder, gastric, pancreatic, head, neck, renal, prostate, colorectal, oesophageal or thyroid cancer, and melanoma.

Different types of cancers may include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, uveal melanoma and breast cancer.

More particularly the peptides described herein (or nucleic acids that encode said peptides) are useful in the treatment of cancers which exhibit a deregulation of PP1 and/or PP2A or which exhibit an over-expression of the anti-apoptotic protein Bcl-2, an apoptotic regulator that interacts with and is controlled by PP1 and PP2A.

High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in leukemias that do not have a t(14; 18) chromosomal translocation, including lymphocytic leukemias of the pre-B cell type, neuroblastomas, nasophryngeal carcinomas, and many adenocarcinomas of the prostate, breast, and colon. Especially overexpression of bcl-2 was found in chronic lymphocytic leukemia (CLL) (Deng et al, 2009; Prickett et al, 2004).

In a preferred embodiment, the cancer tumor is thus a lymphoma, especially a leukemia, such as chronic lymphocytic leukemia (CLL).

Furthermore, the chimeric peptides (or nucleic acids that encode said peptides) may be used for the treatment of metastases.

According to another embodiment, the hyperproliferative disorder may be a non-cancerous hyperproliferative disorder such as benign hyperplasia of the skin (e.g., psoriasis) or prostate (e.g., benign prostatic hypertrophy (BPH)), rheumatoid arthritis, inflammatory bowel disease, osteoarthritis, leiomyomas, adenomas, lipomas, hemangiomas, fibromas, vascular occlusion, restenosis, atherosclerosis, or oral hairy leukoplakia.

The chimeric peptides (or nucleic acids that encode said peptides) as described herein may also be used for treating parasitic diseases.

In particular, the chimeric peptides (or nucleic acids that encode said peptides) may have the ability to decrease the parasite load in a subject of at least 50%, 60%, 70%, 80%, 90% or 100%.

The invention also provides a method of treatment of a parasitic disease in a patient in need thereof, which method comprises administering said patient with a chimeric peptide or a nucleic acid that encode said peptide.

Preferably, the parasitic disease is due to a parasite that belongs to the species *Trypasonoma*, *Theileria* or *Plasmodium*.

The parasitic disease caused by the *Trypanosoma* may be sleeping sickness disease in humans, Chagas disease in humans, Nagana disease in ruminant livestock, horses and pigs, Trypanosomiasis in birds, dourine or covering sickness in horses and other Eauidae.

The parasitic disease caused by *Theileria* may be the tropical theleriosis, the Mediterranean Coast Fever, the East Coast Fever or the equine or ovine piroplasmosis.

The parasitic disease caused by *Plasmodium* may be malaria.

Pharmaceutical Compositions:

The vectors of the invention, in particular chimeric peptides (or nucleic acid that encode said peptide) may be administered by any convenient route including intravenous, oral, transdermal, subcutaneous, mucosal, intramuscular, intrapulmonary, intranasal, parenteral, rectal, vaginal and topical. Intranasal route is of particular interest.

Advantageously, intra-tumoral administration is also contemplated.

The therapeutic agent is formulated in association with a pharmaceutically acceptable carrier.

The pharmaceutical composition may also include, or be combined with any other active principle, such as in particular an anti-cancer agents, e.g. conventional cytotoxic chemotherapies with inhibitors of DNA replication such as DNA binding agents in particular alkylating or intercalating drugs, antimetabolite agents such as DNA polymerase inhibitors, or topoisomerase I or II inhibitors, or with anti-mitogenic agents such as alkaloids. In a further embodiment, the vectors of the invention, in particular chimeric peptides (or nucleic acid that encode said peptide), may be combined with protease (kinase, aromatase, ATPase) inhibitors, monoclonal antibodies or hormones or hormone analogs.

In a preferred embodiment, the therapeutic agent may be administered by electroporation. Electroporation, also known as electropermeabilization or electroinjection, is the permeabilization of cell membranes as a consequence of the application of certain short and intense electric fields across the cell membrane, the cells or the tissues. Typically, electroporation consists of injecting compounds, preferably via intramuscular or intradermal route, followed by applying a series of electric pulses by means of electrodes connected to a generator. The conditions for applying an electric field in the injection zone are now well known to those persons skilled in the art, and are in particular described in the U.S. Pat. No. 5,468,223. Those persons skilled in the art will be able to adapt these conditions according to each case. The electric field may be 50-200 microseconds pulses of high-strength electric fields in the range of 1-5000 V/cm and with a frequency between 0.1 and 1,000 hertz. Typically, a sequence of eight 100 microseconds pulses of 1000-1500 V/cm with a frequency of 1 hertz is applied.

The therapeutic agent, such as the chimeric peptide, is formulated in association with a pharmaceutically acceptable carrier.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product.

The dosing is selected by the skilled person so that a pro-apoptotic effect is achieved, and depends on the route of administration and the dosage form that is used. Total daily dose of the chimeric peptide administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Further aspects and advantages of the present invention will be disclosed in the following experimental section, which should be regarded as illustrative and not limiting the scope of the present application.

EXAMPLES

Example 1

Design and Characterization of Mutated Non-Degradable DPT-C9h Penetrating Peptides 1.1. Materials and Methods Peptide Synthesis and Sequence Peptides were synthesized in an automated multiple peptide synthesizer with solid phase procedure and standard Fmoc chemistry. The purity and composition of the peptides were confirmed by reverse phase HPLC and by amino acid analysis.

Analysis Peptide Stability in Human Serum

Analysis of peptides degradation was done by Proteominer and Maldi-Tof as previously described.

1.2. Results

DPT-C9h is VKKKKIKREIKI-YVETLDDIFEQWAHSEDL, (SEQ ID NO: 6)

The R residue was mutated to K (Mut1-DPT-C9h), N (Mut2-DPT-C9h) or A (Mut3-DPT-C9h).

Figure 1:
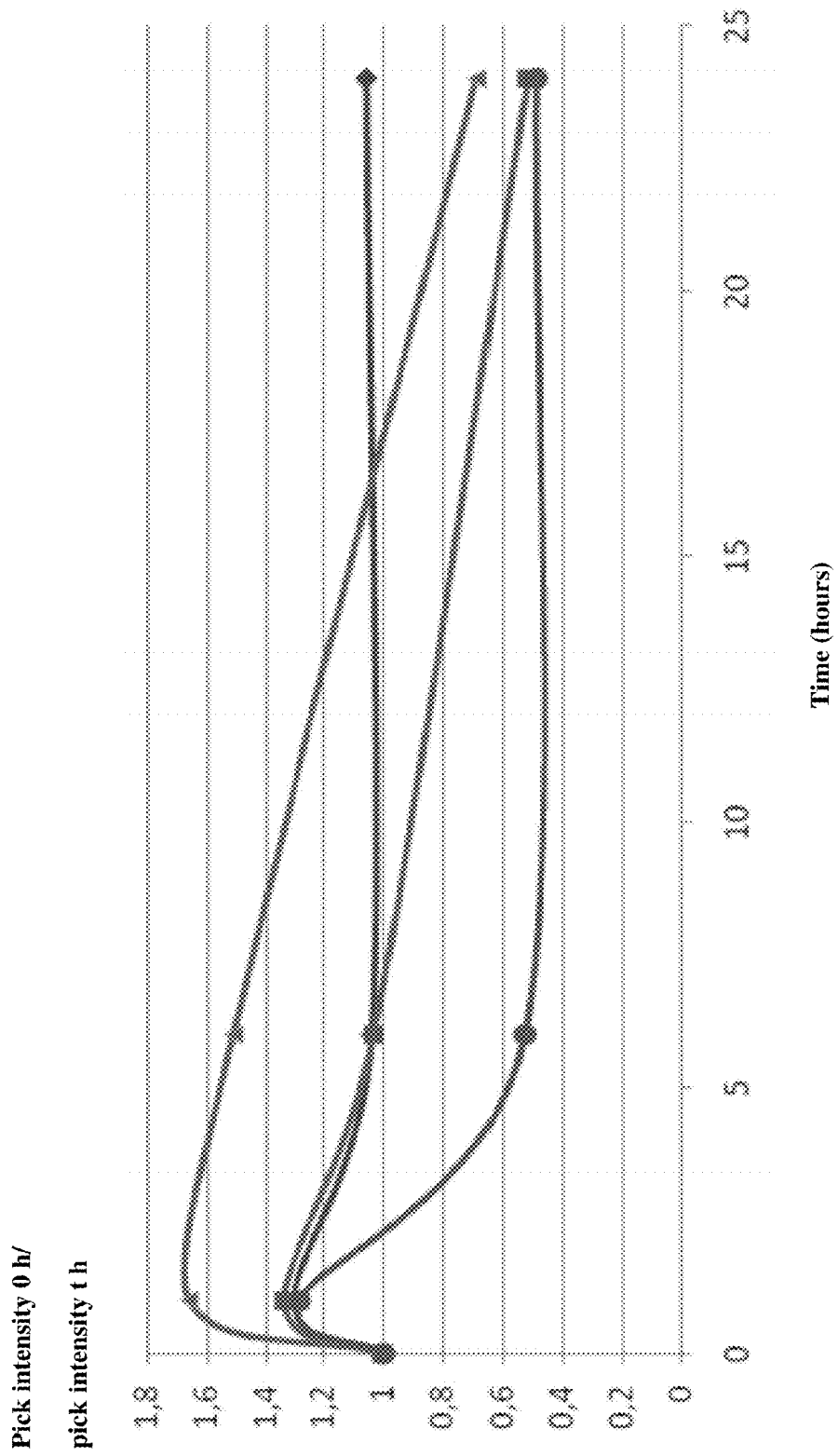
FIG. 1 is a graph that shows stability of the mutated peptides analyzed by Proteominer fractionation and Maldi-Tof. The ratio of intensity of each pick is represented, relative to its own control. The R residue was mutated to K (Mut1-DPT-C9h), N (Mut2-DPT-C9h) or A (Mut3-DPT-C9h). Round: control DPT-C9h peptide (SEQ ID NO:6), Square: Mut1-DPT-C9h, Triangle: Mut2-DPT-C9h, Diamond: Mut3-DPT-C9h.

FIG. 1 shows that Mut3-DPC-C9h peptide is not degraded upon 24h of contact with the human serum. In addition, the other mutants showed a higher stability compared to control peptide (DPT-C9h).

Example 2

Effect of Mutated DPT-C9h on Apoptosis

2.1. Materials and Methods

Cells

Human breast cancer HBCx-12A, cell line has been isolated from primary human cancer xenografts and was cultured in RPMI medium supplemented with 10% of FCS.

Detection of Apoptosis by Annexin-V-FITC Staining

Apoptotic cells were detected using Annexin-V (-FITC from BD biosciences) as described by the manufacturer. Briefly, the cells were washed in 1× binding buffer, centrifugated and then resuspended in 200 µl of 1× binding buffer containing Annexin V-FITC (0.1 µg/ml) and PI (0.5 µg/ml). After incubation at room temperature in the dark for 10 min, cells were analyzed by flow cytometry. Data acquired by FACSCalibur (BD biosciences) were analyzed with Cellquest Pro software.

2.2. Results

Figure 2:
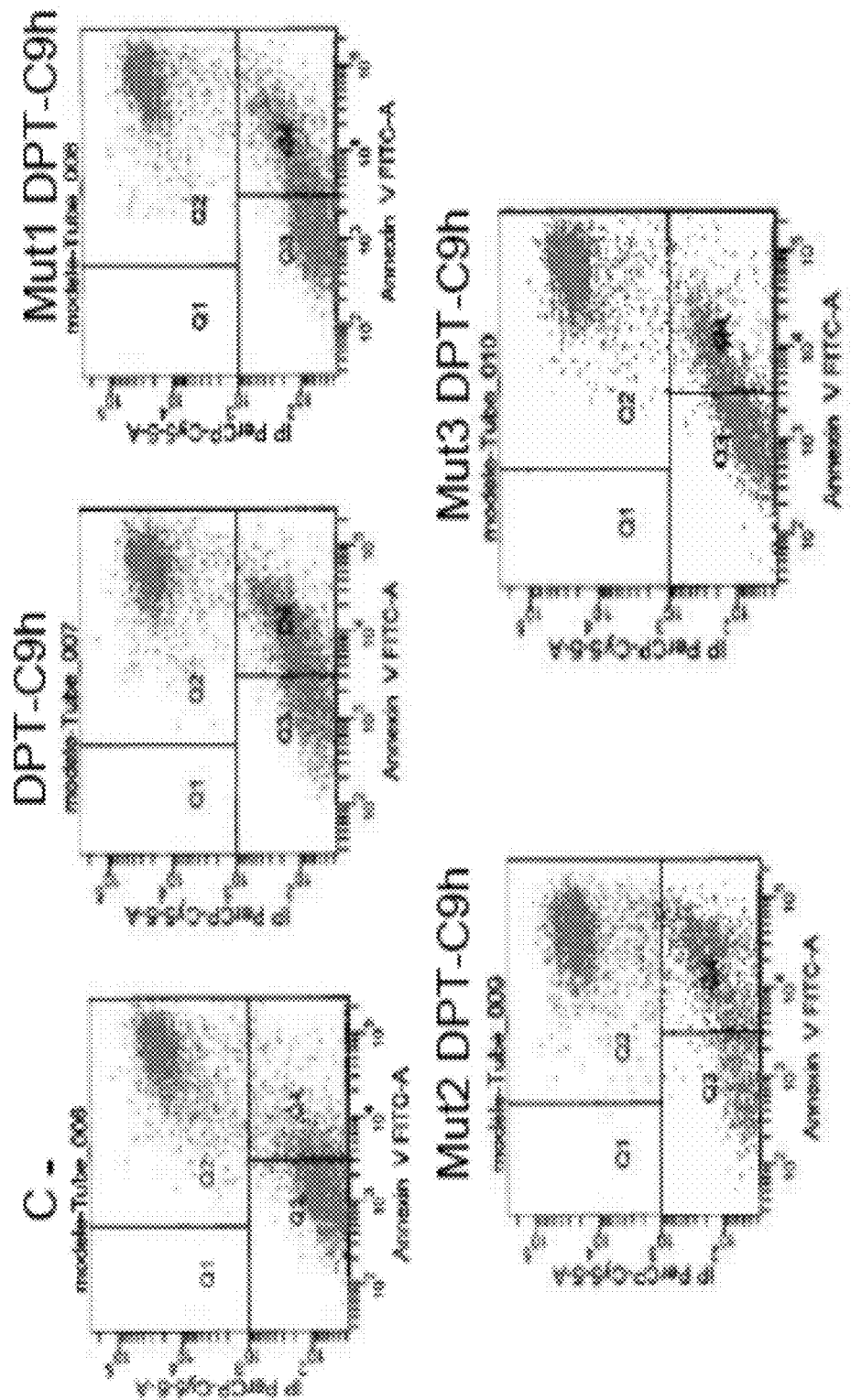
FIG. 2 shows an analysis of apoptosis by annexin-V-FITC staining of breast cancer cell line HBCx-12A was treated for 24h with 100 µM of the control and mutated peptides.

The inventors have then analyzed whether the mutated peptides retain the capacity to induce apoptosis. The breast cancer cell line HBCx-12A was treated for 24h with 100 µM of the control and mutated peptides. Apoptosis was analyzed by annexin-V-FITC staining. As shown in FIG. 2, the analyzed peptides induce similar levels of apoptosis. The same result was observed when using the cell lines HBC-x3 and HBCx-17.

Example 3

Biodistribution of Mut3DPT-C9h in Tumors

4.1. Materials and Methods

Peptide Synthesis and Sequence

Peptides (DPT-C9h and Mut3DPT-C9h) were synthesized as described above. The fluorochrome Cy5 was added during the synthesis of the peptide.

Fluorescence Assays

Mice were IP (intraperitonally)-injected with the peptide Cy5DPT-C9h or Mut3DPT-C9h (5 mg/kg) and then analyzed at different times after injection.

Fluorescence imaging was performed with the IVIS imaging system (IVIS 100, Caliper Life Sciences, USA). Mice were anesthetized upon analysis. Imaging acquisition time was from 1 s to 10 s, depending on the fluorescence signal. Analysis was performed using software Living Image V. 2.50 (Caliper Life Sciences).

4.2. Results

Biodistribution of Mut3DPT-C9h and DPT-C9h in the breast cancer xenograft models.

Figure 3:
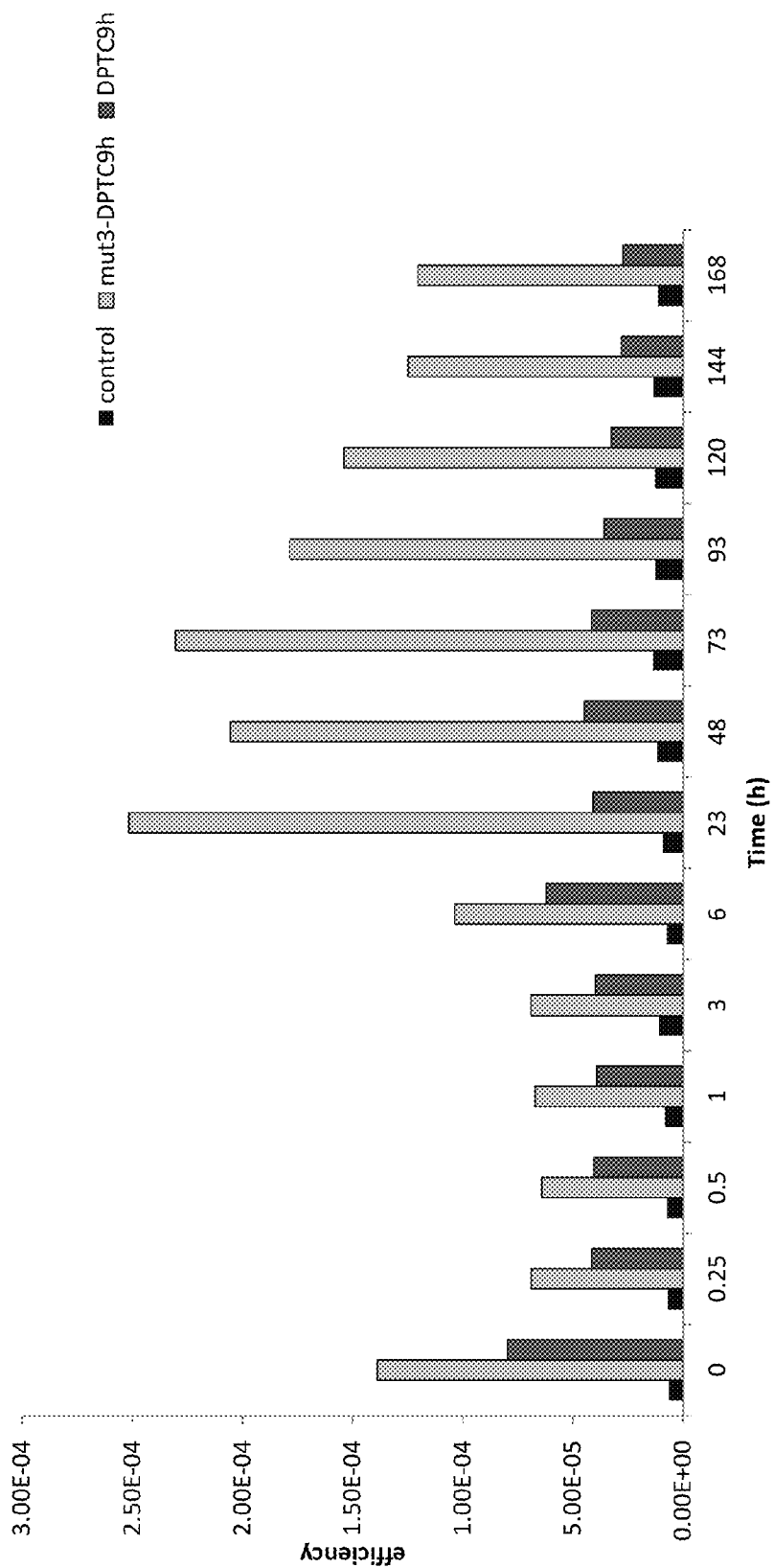
FIG. 3 shows biodistribution of Cy5DPT-C9h and Cy5Mut3DPT-C9h. Mice were grafted in interscapular by luminal breast cancer xenograft HBCx-3. They received one intraperitoneal injection of DPT-C9h or Mut3DPT-C9h labelled with Cy5 at 5 mg/kg. Control mouse received the control excipient (glucose 5%). Mice were imaged between 0 (prior to injection) and 168h after injection. Fluorescence of the tumors was calculated and normalized by using Living Image software.

The inventors were interested in analyzing and comparing the biodistribution of both peptides. FIG. 3 shows the biodistribution of Cy5DPT-C9h and Cy5Mut3DPT-C9h in a breast cancer xenograft model. Mice were intraperitonally (IP) injected and biodistribution analyzed at different times upon injection.

FIG. 3 shows that 6 h after IP injection, the inventors were able to detect both peptides in the tumor. The maximal peak of detection of Cy5 Mut3DPT-C9h is detected 23h after injection, slightly decreasing the intensity of the fluorescence after this time. Finally, considerable level of Cy5Mut3DPT-C9h was detected 168h after injection. The maximum level of Cy5DPT-C9h fluorescence was detected 6h after injection, slightly decreasing after this period of time. Low level of Cy5DPT-C9h was detected upon 168h of treatment.

Taken together, these results show that Cy5-labelled DPT-C9h and Cy5-labelled Mut3DPT-C9h reach the tumor. More importantly, Cy5-labelled Mut3DPT-C9h showed to be more stable that the original peptide, DPT-C9h.

The mutated peptide Mut3DPT-C9h shows a biodistribution in the tumor more sustained than the original peptide (DPT-C9h) since we are able to detect the fluorescence of the Cy5 fluorochrome longer that the fluorescence of DPT-C9h.

This new property will allow to reduce the dose of peptide injected as well as the schedule of administration. In summary, the new mutants have a clear new advantage compared to control peptide and have a new characteristic since they are not degradable by serum proteases.

REFERENCES

Deng X, Gao F, and W. Stratford May. Dephosphorylation and up-regulation of Bcl2-p53 binding Protein phosphatase 2A inactivates Bcl-2's antiapoptotic function by dephosphorylation and up-regulation of Bcl2-p53 binding. Blood. 2009 Jan. 8; 113(2):422-8.

Guergnon, F. Dessauge, V. Dominguez, J. Viallet, X. Cayla, A. Rebollo, V. Yuste, S. Susin, P E. Bost and A. Garcia Use of penetrating peptides interacting with PP1/PP2A proteins as a basis for a new Drug Phosphatase Technology. Mol. Pharmacol. (2006) 69:1115-1124.

Lehninger, (1975) Biochemistry, Second Edition, Worth Publishers, Inc. New-York N.Y., pp. 71-77.

Pitton, C., Rebollo, A., Van Snick, J., Theze, J. and Garcia, A. (1993) High affinity and intermediate affinity forms of the human IL-2 receptor expressed in an IL-9-dependent murine T cell line deliver proliferative signals via differences in their transduction pathways. Cytokine, 5, 362-371.

Prickett T D, and Brautigan D (2004). Ovelapping binding sites in Protein Phosphatase 2A for association with regulatory 1 and a4 (mTap42) subunits. J. Biol. Chem. 279, 38912-38920.

Walensky et al, Science, 2004, 305:1466-1470

The invention claimed is:

1. A vector comprising a penetrating peptide consisting of the amino acid sequence VKKKKIKAEIKI (SEQ ID NO:2) coupled to a therapeutic agent.

2. The vector of claim 1, wherein the vector is a chimeric peptide construct.

3. The vector of claim 1, wherein the therapeutic agent is selected from the group consisting of a cytotoxic agent, an anti-viral agent, an anti-bacterial agent, and an anti-parasitic agent.

4. The vector of claim 3, wherein the cytotoxic agent is a pro-apoptotic peptide.

5. The vector of claim 4, wherein the penetrating peptide is fused to the pro-apoptotic peptide, and the vector is 23 to 70 amino acids in length.

6. The vector of claim 4, wherein the penetrating peptide is fused to the pro-apoptotic peptide at the C-terminus of the penetrating peptide.

* * * * *

SEQUENCE LISTING

<160> NUMBER OF SEQ ID NOS: 18

<210> SEQ ID NO 1
<211> LENGTH: 11
<212> TYPE: PRT

```
<213> ORGANISM: Artificial Sequence
<220> FEATURE:
<223> OTHER INFORMATION: cell penetrating peptide
<220> FEATURE:
<221> NAME/KEY: MISC_FEATURE
<222> LOCATION: (1)..(1)
<223> OTHER INFORMATION: Xaa is vacant, is a lysine residue, or valine-
      lysine
<220> FEATURE:
<221> NAME/KEY: MISC_FEATURE
<222> LOCATION: (7)..(7)
<223> OTHER INFORMATION: Xaa is an amino acid residue that is different
      from arginine and is non-conservative with respect to arginine
<220> FEATURE:
<221> NAME/KEY: MISC_FEATURE
<222> LOCATION: (10)..(10)
<223> OTHER INFORMATION: Xaa is vacant, is a lysine residue, or lysine-
      isoleucine
<220> FEATURE:
<221> NAME/KEY: MISC_FEATURE
<222> LOCATION: (11)..(11)
<223> OTHER INFORMATION: Xaa is vacant or is an amino acid sequence of
      one to 4 amino acids

<400> SEQUENCE: 1

Xaa Lys Lys Lys Ile Lys Xaa Glu Ile Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 2

Val Lys Lys Lys Lys Ile Lys Ala Glu Ile Lys Ile
1               5                   10

<210> SEQ ID NO 3
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: MISC_FEATURE
<222> LOCATION: (2)..(2)
<223> OTHER INFORMATION: Xaa is valine or isoleucine
<220> FEATURE:
<221> NAME/KEY: MISC_FEATURE
<222> LOCATION: (7)..(7)
<223> OTHER INFORMATION: Xaa is aspartic acid or glycine
<220> FEATURE:
<221> NAME/KEY: MISC_FEATURE
<222> LOCATION: (9)..(9)
<223> OTHER INFORMATION: Xaa is phenylalanine or leucine
<220> FEATURE:
<221> NAME/KEY: MISC_FEATURE
<222> LOCATION: (14)..(14)
<223> OTHER INFORMATION: Xaa is arginine or histidine
<220> FEATURE:
<221> NAME/KEY: MISC_FEATURE
<222> LOCATION: (16)..(16)
<223> OTHER INFORMATION: Xaa is vacant or is glutamate, or glutamate-
      aspartate, or glutamate-aspartate-leucine

<400> SEQUENCE: 3

Tyr Xaa Glu Thr Leu Asp Xaa Ile Xaa Glu Gln Trp Ala Xaa Ser Xaa
1               5                   10                  15

<210> SEQ ID NO 4
<211> LENGTH: 30
```

```
<212> TYPE: PRT
<213> ORGANISM: Artificial Sequence
<220> FEATURE:
<223> OTHER INFORMATION: cell penetrating peptide

<400> SEQUENCE: 4

Val Lys Lys Lys Lys Ile Lys Ala Glu Ile Lys Ile Tyr Val Glu Thr
1               5                   10                  15

Leu Asp Asp Ile Phe Glu Gln Trp Ala His Ser Glu Asp Leu
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 5

Val Lys Lys Lys Lys Ile Lys Ala Glu Ile Lys Ile Tyr Ile Glu Thr
1               5                   10                  15

Leu Asp Asp Ile Leu Glu Gln Trp Ala Arg Ser Glu Asp Leu
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 6

Val Lys Lys Lys Lys Ile Lys Arg Glu Ile Lys Ile Tyr Val Glu Thr
1               5                   10                  15

Leu Asp Asp Ile Phe Glu Gln Trp Ala His Ser Glu Asp Leu
            20                  25                  30

<210> SEQ ID NO 7
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 7

Val Lys Lys Lys Lys Ile Lys Arg Glu Ile Lys Ile
1               5                   10

<210> SEQ ID NO 8
<211> LENGTH: 20
<212> TYPE: PRT
<213> ORGANISM: Artificial Sequence
<220> FEATURE:
<223> OTHER INFORMATION: cell penetrating peptide

<400> SEQUENCE: 8

Asp Thr Leu Asp His Ile Arg Ala Leu Asp Arg Leu Gln Glu Val Pro
1               5                   10                  15

His Glu Gly Pro
            20

<210> SEQ ID NO 9
<211> LENGTH: 20
<212> TYPE: PRT
<213> ORGANISM: Artificial Sequence
```

<220> FEATURE:
<223> OTHER INFORMATION: cell penetrating peptide

<400> SEQUENCE: 9

Asp Thr Leu Asp His Ile Arg Ala Leu Asp Arg Leu Gln Glu Val Pro
1               5                   10                  15

His Glu Gly Pro
            20

<210> SEQ ID NO 10
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 10

Val Lys Lys Lys Lys Ile Lys Lys Glu Ile Lys Ile
1               5                   10

<210> SEQ ID NO 11
<211> LENGTH: 12
<212> TYPE: PRT
<213> ORGANISM: Artificial Sequence
<220> FEATURE:
<223> OTHER INFORMATION: cell penetrating peptide

<400> SEQUENCE: 11

Val Lys Lys Lys Lys Ile Lys Asn Glu Ile Lys Ile
1               5                   10

<210> SEQ ID NO 12
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 12

Val Lys Lys Lys Lys Ile Lys Lys Glu Ile Lys Ile Tyr Val Glu Thr
1               5                   10                  15

Leu Asp Asp Ile Phe Glu Gln Trp Ala His Ser Glu Asp Leu
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 13

Val Lys Lys Lys Lys Ile Lys Lys Glu Ile Lys Ile Tyr Ile Glu Thr
1               5                   10                  15

Leu Asp Asp Ile Leu Glu Gln Trp Ala Arg Ser Glu Asp Leu
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 14

Val Lys Lys Lys Lys Ile Lys Asn Glu Ile Lys Ile Tyr Val Glu Thr
1               5                   10                  15

Leu Asp Asp Ile Phe Glu Gln Trp Ala His Ser Glu Asp Leu
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: cell penetrating peptide

<400> SEQUENCE: 15

Val Lys Lys Lys Lys Ile Lys Asn Glu Ile Lys Ile Tyr Ile Glu Thr
1               5                   10                  15

Leu Asp Asp Ile Leu Glu Gln Trp Ala Arg Ser Glu Asp Leu
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: chimeric peptide

<400> SEQUENCE: 16

Val Lys Lys Lys Lys Ile Lys Ala Glu Ile Lys Ile Asp Thr Leu Asp
1               5                   10                  15

His Ile Arg Ala Leu Asp Arg Leu Gln Glu Val Pro His Glu Gly Pro
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: chimeric peptide

<400> SEQUENCE: 17

Val Lys Lys Lys Lys Ile Lys Lys Glu Ile Lys Ile Asp Thr Leu Asp
1               5                   10                  15

His Ile Arg Ala Leu Asp Arg Leu Gln Glu Val Pro His Glu Gly Pro
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: chimeric peptide

<400> SEQUENCE: 18

Val Lys Lys Lys Lys Ile Lys Asn Glu Ile Lys Ile Asp Thr Leu Asp
1               5                   10                  15

His Ile Arg Ala Leu Asp Arg Leu Gln Glu Val Pro His Glu Gly Pro
            20                  25                  30